United States Patent [19]

Soltis et al.

[11] Patent Number: 5,707,669
[45] Date of Patent: Jan. 13, 1998

[54] YEAST COMPOSITION

[75] Inventors: John Soltis, Alpharetta, Ga.; Joseph L. Sell, Beaver Dam, Wis.

[73] Assignee: M-CAP Technologies International, Wilmington, Del.

[21] Appl. No.: 712,004

[22] Filed: Sep. 11, 1996

[51] Int. Cl.⁶ .............................. A23L 1/28; A21D 8/04; A23B 5/00
[52] U.S. Cl. .................. 426/62; 486/60; 486/61; 486/89; 486/96; 426/98; 426/99
[58] Field of Search ...................... 426/62, 60, 61, 426/89, 96, 98, 99

[56] References Cited

U.S. PATENT DOCUMENTS

| | | | |
|---|---|---|---|
| 4,001,480 | 1/1977 | Shank | 428/411 |
| 4,647,538 | 3/1987 | Mosbach et al. | 435/177 |
| 4,719,114 | 1/1988 | Percel | 426/62 |

*Primary Examiner*—Michael P. Woodward
*Assistant Examiner*—Brenda Glass Brumback

[57] ABSTRACT

Encapsulated yeast composition especially developed for use with frozen doughs comprising food grade fibers having adsorbed thereon liquid cream yeast, the particles being coated with a continuous layer of impervious thermoplastic material, frozen dough containing the encapsulated yeast composition and the method for making the encapsulated yeast.

12 Claims, No Drawings

YEAST COMPOSITION

FIELD OF INVENTION

The invention is directed to a yeast composition. In particular, the invention is directed to an encapsulated yeast composition especially developed for use with frozen doughs. The invention is also directed to the method for making the encapsulated yeast product.

BACKGROUND OF THE INVENTION

In recent years, a very large market has developed for "frozen baked goods," that is, bread products which are baked from frozen doughs. Such goods include breads and rolls, croissants, pies, cakes, cookies, Danish rolls and similar sweet goods and doughnuts.

The widest application of frozen doughs is in the preparation of frozen doughs and batters for various bakery foods in commercial bakeries or plants which are dedicated to the production of such products. In these facilities, dough products are fully formed and distributed in the frozen state to retail outlets, such as supermarkets, where they are thawed, proofed if needed, and baked on the premises for direct sale to the consumer. This method of distribution is quite desirable since it offers customers freshly baked products with all the desirable properties of fresh bakery goods, including taste, smell and texture.

An ongoing problem with the use of frozen doughs in this manner is that the frozen doughs slacken and deteriorate during prolonged storage, which results in longer proof times, decreased bake volumes and poorer grain and texture. Though these problems are in part due to the diminished gas holding properties of the frozen dough, they are also caused, in substantial part, by decreased viability and activity of the yeast. For example, the potency of the yeast is reduced by 50% or more upon storage for as little as 2–3 weeks.

Several technical approaches to compensate for this loss of yeast viability have been tried with varying degrees of success: (1) reformulation of the frozen doughs; (2) use of only high quality flour, for example, flour having a protein level of 12.5–13.5% supplemented with wheat gluten; (3) more rapid freezing as a trade-off between optimizing yeast cell viability and minimizing damage to the dough structure; (4) increasing the yeast level as much as two times; and (5) research into superior yeast strains having inherent resistance to freezing. The most extensively studied ingredient of frozen doughs has been the yeast itself, which is the ingredient necessary to provide proper gas production for dough leavening and lend character and flavor to the finished bread product.

While all of these approaches have merit, none is seen to be the sole answer to the problem of yeast deactivation and they are all quite long range in their scope. Therefore, a need remains for a method by which the action of the yeast can be controlled with better regard for both the freezing and bake-off environment in which the yeast acts.

SUMMARY OF THE INVENTION

To overcome the difficulties associated with the use of yeast in frozen baked goods, the invention is directed to a yeast composition comprising finely divided free-flowing particles, each containing a plurality of food grade fibers having adsorbed thereon cream yeast, the particles being coated with a continuous layer of moisture-impervious thermoplastic material.

In a second aspect, the invention is directed to a frozen dough composition comprising flour, water, salt and the above-described encapsulated yeast containing particles.

In a further aspect of the invention, it is directed to a method for making the above-described composition comprising the sequential steps:

(1) providing finely divided particles of food grade fiber having an average particle size of 50–1000 micrometers;
(2) with continuous agitation by which the surfaces of the fiber particles are repetitively exposed, intermittently applying liquid cream yeast onto the exposed surfaces of the fiber (a) in a total amount to adsorb the liquid cream yeast to a preselected level and (b) at a rate such that the particles remain free-flowing;
(3) with continuous agitation by which the surfaces of the fiber containing adsorbed cream yeast are repetitively exposed, intermittently spraying molten thermoplastic material onto the exposed surface of the fiber particles (a) in a total amount sufficient to form a continuous coating thereon, (b) at a rate such that the particles remain free-flowing and (c) the interval between spraying cycles is sufficient to effect solidification of the coating material on the particles before any further spraying.

DETAILED DESCRIPTION OF THE INVENTION

The advantages of the yeast composition of the invention are five-fold: (1) unlike ordinary cream yeast, the encapsulated cream yeast need not be refrigerated; (2) the encapsulated cream yeast has a longer shelf life even without refrigeration; (3) it increases the shelf life of the frozen dough in which it is used; (4) the effectiveness of the yeast is enhanced because it is released at a later time in the baking process; and (5) the effectiveness of the yeast is further enhanced because an adequate amount of moisture, which is essential to the yeast's activity, is available to the yeast in situ upon release.

A. Adsorbent Fibers

Suitable adsorbents for use in the invention are food grade fibers such as those derived from cereals. For example, the non-digestible fibers derived from oat hulls, rice hulls, soy bean hulls, field pea hulls, wheat bran, corn bran, corn cobs, beet pulp, wheat straw, oat straw, bagasse, cellulosic dietary fibers and the like are suitable adsorbents for use in the invention. Mixtures of such fibers can also be used. It is not required that the fibers be bleached for use in the invention. It will be recognized that the fibers for use in the invention must be of suitable grade so that they meet regulatory standards for use in foods in whatever country they are used. In the United States, they must have FDA approval for use in food or have GRAS status.

It will be recognized that the adsorption capability of such dietary fibers will vary widely. However, this property is easily determined by comparative testing with a given cream yeast. Oat hulls, however, appear to have higher adsorption properties than most other food grade fibers.

Before treating the fiber particles to effect adsorption of the liquid cream yeast thereon, the fibers will be ground as necessary to bring their average particle size within the range of 50–1000 micrometers.

B. Adsorbate Cream Yeast

The adsorbate material for use in the invention is liquid cream yeast, which is a baker's yeast in the form of a flowable liquid dispersion of yeast in water. Such cream yeasts contain 15–30% yeast dispersed in 85–70% water. The viscosity of the cream yeast is such that it can be stored at 34°–39° F. (1°–4° C.) and pumped and metered into a dough mixer. Any yeast suitable for making yeast-raised products can be converted to cream form by grinding the solid yeast in water to disperse the yeast in the form of finely divided particles. Commercially available cream yeasts can also be used in the invention with similar effectiveness at equivalent concentrations. However, conventional dried yeast and vacuum-packed compressed yeast are not suitable for use in the invention, unless they can be converted to cream form without loss of activity.

The amount of cream yeast which can be adsorbed by the fiber without agglomerating the fibers will vary widely, depending on the type of yeast, the kind of fiber used and the condition of the fiber. Applicants' experience indicates that most fibers will adsorb, at most, no more than about 32% wt. cream yeast at room temperature.

It is preferred to carry out the method for making the encapsulated particles of the invention at a temperature no higher than room temperature (ca. 68° F., 20° C.) in order to minimize deactivation of the yeast during the encapsulation procedure, and to extend the shelf life of the composition prior to use. It is also preferred that the fiber particles contain as much cream yeast as can be adsorbed without deteriorating the free-flowing nature of the particles. In practice, it will be preferred to adsorb the cream yeast to a preselected level which approximates the maximum level of cream yeast which can be adsorbed by the fiber particles at the chosen operating conditions. However, it is important that the amount of cream yeast not exceed that which can be truly adsorbed in the fiber particles. The reason for this is that, if the adsorbent particles are coated with cream yeast beyond that amount which is adsorbed on the fiber, the unadsorbed yeast tends to be released prematurely during the baking process. To avoid this phenomenon entirely, it is preferred that no more than 28% wt. cream yeast be adsorbed on the fibers. About 24% wt. cream yeast appears to be optimum. It is preferred, however, that at least 15% wt. cream yeast be adsorbed on the fiber particles. A cream yeast adsorption level of 18–24% wt. is preferred from the standpoint of maintaining the product in free-flowing form.

C. Impervious Coating Material

Coating materials suitable for use in the invention (1) must be thermoplastic, (2) must be inert with respect to the underlying fiber and yeast, and (3) must form a moisture-impervious film thereon. The coating material must be impervious to aqueous fluids in order to prevent premature activity of the yeast. Furthermore, because the yeast compositions of the invention are for use in human food, it will be recognized that the coating must be safe for human consumption. Thus, in the United States the coating must comply with appropriate regulations of the U.S. Food & Drug Administration. Hydrogenated vegetable oils, such as soybean oil and cottonseed oil, are particularly suited for use in the invention. Other coating materials, which are operationally suitable for use in the invention, include mono and di-glycerides, bees wax, paraffin wax, microcrystalline wax, sunflower seed fats, organic acids, synthetic waxes, hydrogenated castor oil and poly(vinyl alcohol), hydrogenated tallow and animal fats, substituted bees wax, synthetic paraffin wax, stearates, glyceral tristearate, crystalline polyethylene and poly(ethylene glycol). As mentioned above, such coating materials must comply with relevant FDA Regulations in the United States. Coating materials are selected primarily on the basis of their melting points and release characteristics. Mixtures of such shell materials can also be used to impart particular combinations of physical properties to the encapsulated particles.

For the purposes of the invention, it is preferred that the thermoplastic coating material soften at 125°–128° F. (52°–53° C.), and become completely molten at a temperature no higher than 138° F. (59° C.). In addition, it is essential that the coating remains at least moderately non-friable and preferably flexible at minus 32°C. to prevent premature release of the yeast arising from fracture of the coating during handling of the frozen dough. The thickness of the thermoplastic coating is not critical, but it is preferred to be 10–800 micrometers. The minimum thickness cited above is needed to assure continuity of the coating of the fiber particles. A still higher level of 150 micrometers is further preferred. On the other hand, the shell thickness should not exceed 800 micrometers, and preferably 550 micrometers, lest the encapsulated particles become less granular and thus lose their free-flowing character. It is, of course, preferred that the particles be free-flowing in bulk, so that they can be dispersed more easily in the dough.

Secondary dough additives may be added to the coating material without adversely affecting the basic functional properties of the coating. Such shell loading materials include ascorbic acid and ammonium and alkali metal carbonates. The former materials are particularly suitable as replacements for potassium bromate. The latter are added as leavening agents. In both instances, the compounds are admixed with the adsorbed fibers in the form of finely divided particles, in amounts corresponding to 0.1–10% wt., basic total particle weight prior to encapsulation. The coating of the encapsulated particles thus contains, dispersed therein, both adsorbed fibers and secondary additive particles.

D. Process Variables

An important aspect of the invention is that the encapsulation must be carried out in such manner that the final product is of powder consistency, and does not contain lumps having paste-like consistency. This goal is attained during application of the cream yeast by adjusting the rate at which the liquids are applied. Thus, if the admixture incurs lumps or becomes paste-like during application of the cream yeast onto the fiber, it can be returned to free-flowing powder consistency by slowing down the rate of cream yeast application, or by stopping cream yeast addition for a short time while continuing mixing. Likewise, the problem can be handled in the same manner during spraying of the thermoplastic coating onto the fibers containing the adsorbed cream yeast. The cream yeast can be applied to the fiber particles by either spraying, which is the preferred method, or by controlled gravity feed.

The method of the invention can be easily carried out in conventional mixing equipment that is used for liquid-solid systems. In general, batch mixing equipment such as stationary tank mixers, shear bar mixers, helical blade mixers, double-arm kneading mixers and ribbon blenders can be used. Double-arm mixers, such as sigma mixers, have been found to be particularly satisfactory for the practice of the invention. Such mixers provide thorough, uniform mixing at a controlled rate of shear; yet, blade clearances can be adjusted to avoid fracture of the finely divided fiber particles.

Because of the necessity of monitoring the mixing process as described above, it is preferred to employ mixers in which the physical state of the material being mixed can be observed visually and periodic additions can be made as needed.

In order to reduce deactivation of the yeast, it is preferred that the entire encapsulation process be carried out at a comparatively low temperature, e.g. room temperature. Even lower temperatures are desirable, but are less practicable because of heat transfer from the molten coating material.

The spraying steps, in which the thermoplastic coating is applied to the fiber particles containing adsorbed cream yeast, are carried out in such manner that the coating material is heated to above its melting point and sprayed onto the fibers in molten form. Because of the difference between the temperature of the fibers and the molten coating material, the coating material solidifies rapidly. Thus, the coating is applied to the fiber particles in a plurality of steps in which a thin coating is applied and rapidly solidified by contact with the relatively cool fibers before the next spraying step. It is, however, preferred to minimize the difference between the temperature of the coating and the fiber particles in order to avoid too rapid crystallization of the of coating.

The shelf life of frozen doughs containing conventional yeast products is only 2–3 weeks. However, the shelf life of frozen doughs containing the encapulated cream yeast of the cream yeast of the invention is extended to the point that it is onset of freezer burn. Freezer burn of frozen doughs is usually experienced after 3–4 weeks' storage. Furthermore, when encapsulated cream yeast is made in accordance with the invention, its shelf life upon storage at ambient temperature is at least several months.

EXAMPLES

Example 1

This Example shows the laboratory scale preparation of the liquid cream yeast which was used in the further examples set out below. Conventional dry yeast and water were added to an Osterizer(R) blender in weight proportions of 18/82 yeast/water and agitated for 10 minutes. This yielded a stable dispersion of fine yeast particles in the water. Up to this point, the process was conducted at room temperature. If the resultant cream yeast was used immediately, it was encapsulated in the manner described hereinbelow without cooling. On the other hand, if encapsulation was delayed more than a few hours, it was cooled and stored at a temperature of 4°C. in order to retard the metabolic activity of the yeast.

Example 2

A measured amount of dry, free-flowing, ground oat hulls was placed in a sigma mixer, and the hulls were subjected to mixing at a blade speed of 70 rpm. Cream yeast of the above-described composition was then applied by spraying onto the exposed surfaces of the ground oat hulls. Spraying was interrupted as the particles began to agglomerate, and was resumed in each instance after a short time as the yeast adsorbed into the oat hull particles and the free-flowing character of the particles returned. While continuing mixing, the free-flowing oat hulls, containing adsorbed cream yeast, were encapsulated by spraying them with molten cottonseed oil flake. The spraying was conducted in four steps in order to maintain the granular character of the particles. The resultant product consisted of discrete, free-flowing, low-density particles, which were off-white in color. Upon subsequent testing, the yeast was found to have retained all its activity after more than 60 days' storage at room temperature. Likewise, when the encapsulated cream yeast particles were incorporated into a dough and the dough was frozen, it was found that the yeast was fully active, even after 60 days' storage.

What is claimed is:

1. An encapsulated yeast composition comprising finely divided, free-flowing particles, each containing a plurality of food grade fibers having adsorbed thereon liquid cream yeast, the adsorbent particles being coated with a continuous layer of moisture-impervious thermoplastic material.

2. The composition of claim 1, in which the size of the coated particles is 50–1000 micrometers.

3. The composition of claim 1, in which the impervious thermoplastic material is a hydrogenated vegetable oil.

4. The composition of claim 1, in which the amount of adsorbed cream yeast is at the maximum adsorption level of the fiber.

5. The composition of claim 1, in which the fibrous adsorbent material is ground oat hulls.

6. The composition of claim 1, in which the liquid cream yeast is comprised of 15–30% yeast and 85–70% water.

7. The composition of claim 1, in which the moisture-impervious thermoplastic material layer contains dispersed therein finely divided particles of ascorbic acid.

8. The composition of claim 1, in which the impervious material layer contains finely divided particles of alkali metal or ammonium carbonate.

9. The composition of claim 8, in which a mixture of finely divided particles of ascorbic acid and alkali metal carbonate or ammonium carbonate are contained in the impervious layer.

10. The composition of claim 1 in which the moisture-impervious thermoplastic coating layer has a thickness of 10–800 micrometers.

11. A frozen dough composition comprising a mixture of flour, water, salt and yeast, characterized in that the yeast component is an encapsulated yeast composition comprised of finely divided free-flowing particles, each containing a plurality of food grade fibers, having adsorbed thereon liquid cream yeast, the adsorbent particles being coated with a continuous layer of moisture-impervious thermoplastic material.

12. A method for making encapsulated yeast comprising the sequential steps:

(1) providing finely divided particles of food grade fiber having a particle size of 50–1000 micrometers;

(2) with continuous agitation by which the surfaces of the fiber particles are repetitively exposed, intermittently spraying liquid cream yeast onto the exposed surfaces of the fiber (a) in a total amount to adsorb the liquid cream yeast to a preselected level, and (b) at a rate such that the particles remain free-flowing;

(3) with continuous agitation by which the surfaces of the fiber particles are repetitively exposed, intermittently spraying molten thermoplastic material onto the exposed surfaces of the fiber particles (a) in a total amount sufficient to form a continuous coating thereon, (b) at a rate such that the particles remain free-flowing, and (c) the interval between spraying cycles is sufficient to effect solidification of the coating material on the particles before any further spraying.

* * * * *